(12) United States Patent
Ito

(10) Patent No.: US 10,330,635 B2
(45) Date of Patent: Jun. 25, 2019

(54) GAS SENSOR INCLUDING SENSOR ELEMENT, HOUSING AND ELEMENT COVER

(71) Applicant: DENSO CORPORATION, Kariya, Aichi-pref. (JP)

(72) Inventor: Makoto Ito, Kariya (JP)

(73) Assignee: DENSO CORPORATION, Kariya (JP)

( * ) Notice: Subject to any disclaimer, the term of this patent is extended or adjusted under 35 U.S.C. 154(b) by 122 days.

(21) Appl. No.: 15/322,916

(22) PCT Filed: Jun. 5, 2015

(86) PCT No.: PCT/JP2015/066382
§ 371 (c)(1),
(2) Date: Dec. 29, 2016

(87) PCT Pub. No.: WO2016/002438
PCT Pub. Date: Jan. 7, 2016

(65) Prior Publication Data
US 2017/0138896 A1    May 18, 2017

(30) Foreign Application Priority Data

Jun. 30, 2014   (JP) ................................ 2014-133481

(51) Int. Cl.
G01N 27/407    (2006.01)
G01N 27/406    (2006.01)
G01N 27/409    (2006.01)

(52) U.S. Cl.
CPC ....... *G01N 27/4078* (2013.01); *G01N 27/409* (2013.01); *G01N 27/4067* (2013.01);
(Continued)

(58) Field of Classification Search
CPC ............ G01N 27/407; G01N 27/4072; G01N 27/4077; G01N 27/4078
See application file for complete search history.

(56) References Cited

U.S. PATENT DOCUMENTS 3,909,385 A * 9/1975 Spielberg ............ F02D 41/1454
                                                         204/426
4,950,380 A * 8/1990 Kurosawa .......... G01N 27/4072
                                                         204/406

(Continued)

FOREIGN PATENT DOCUMENTS

JP          10-10084       1/1998
JP          2012-21895     2/2012

*Primary Examiner* — Alexander S Noguerola
(74) *Attorney, Agent, or Firm* — Nixon & Vanderhye P.C.

(57) ABSTRACT

A gas sensor is provided with: a sensor element having a solid electrolyte body, a measurement electrode and a reference electrode; a housing into which the sensor element is inserted; and an element cover arranged at the tip-end side of the housing. The element cover has an inner cover arranged so as to cover the tip-end portion of the sensor element from outside, and an outer cover arranged so as to cover the inner cover from outside. When L is defined as an axial distance from a base end of an internal space of the inner cover to the base end of the measurement electrode, an axial distance M from the base end of the internal space of the inner cover to the base end of an inner vent hole positioned in the most base-end side among the inner vent holes provided to the inner cover is 0.2L to 0.65L.

6 Claims, 5 Drawing Sheets

(52) U.S. Cl.
CPC ..... *G01N 27/4071* (2013.01); *G01N 27/4076* (2013.01); *G01N 27/4077* (2013.01)

(56) References Cited

U.S. PATENT DOCUMENTS

| | | | |
|---|---|---|---|
| 6,279,376 B1 * | 8/2001 | Yamada | G01N 27/4077 73/23.2 |
| 2002/0191068 A1 | 12/2002 | O'Hara et al. | |
| 2005/0241368 A1 * | 11/2005 | Yamauchi | G01N 27/407 73/31.05 |
| 2013/0075256 A1 | 3/2013 | Saitou et al. | |
| 2013/0152350 A1 | 6/2013 | Saitou et al. | |

* cited by examiner

GAS SENSOR INCLUDING SENSOR ELEMENT, HOUSING AND ELEMENT COVER

This application is the U.S. national phase of International Application No. PCT/JP2015/066382 filed Jun. 5, 2015, which designated the U.S. and claims priority to JP Patent Application No. 2014-133481 filed Jun. 30, 2014, the entire contents of each of which are hereby incorporated by reference.

BACKGROUND OF THE INVENTION

Technical Field

The present disclosure relates to a gas sensor capable of detecting a specific gas concentration in a gas to be measured.

Background Art

Internal combustion engines or the like for vehicles have an exhaust system in which a gas sensor is arranged to detect a specific gas concentration (e.g. an oxygen concentration) in a gas to be measured such as an exhaust gas. Such a gas sensor includes a sensor element, a housing and an element cover. The sensor element has a solid electrolyte body, and a measurement electrode and a reference electrode respectively provided to one surface and the other surface of the electrolyte body. The housing is inserted with the sensor element. The element cover is arranged at the tip-end side of the housing. For example, JP-A-2000-171429 discloses a gas sensor having an element cover which is made up of an inner cover arranged so as to cover the tip-end side of a sensor element from outside, and an outer cover arranged so as to cover the inner cover from outside.

The gas sensor is attached to an exhaust pipe or the like of the internal combustion engine in a mounting screw portion formed in the housing. The gas sensor has a portion which is closer to the tip-end side than the housing is, and arranged in a channel of the gas to be measured, and a portion which is closer to the base-end side than the housing is, and arranged outside the channel. For this reason, a sealing member filled with talc or the like is provided between the sensor element and the housing in order to ensure airtightness.

CITATION LIST

Patent Literature

[PTL 1] JP-A-2000-171429

However, if the airtightness of a seal portion arranged between the sensor element and the housing is low, air (atmospheric air) may leak from the portion toward the tip-end side of the housing. Accordingly, the air penetrates into the inside of the inner cover. As the air further moves toward the tip-end side in the inner cover, the oxygen concentration in the gas to be measured may be changed in the vicinity of the measurement electrode of the sensor element. Consequently, an error may occur in the specific gas concentration detected by the gas sensor.

More specifically, for example, when the gas sensor measures the exhaust gas of an air-fuel mixture having an ideal air-fuel ratio, that is, an exhaust gas that should have a stoichiometric air-fuel ratio, a value deviated from the stoichiometric air-fuel ratio may be measured due to the influence of the air leakage. Thus, use of the gas sensor for the feedback system of the internal combustion engine may cause erroneous operation of the control system.

In this regard, it is desired that the airtightness is improved in the seal portion. However, completely preventing the air leakage is difficult. Thus, only enhancing the air tightness of the seal portion is not a sufficient measure in the case where more accurate detection of the specific gas is required.

Hence it is desired to provide a gas sensor capable of reducing the influence of the air leakage in the seal portion arranged between a sensor element and a housing, and improving detection accuracy.

An aspect of the present disclosure is a gas sensor characterized in that the gas sensor includes: a sensor element including a solid electrolyte body having oxygen ion conductivity, and a measurement electrode and a reference electrode respectively provided to one surface and the other surface of the solid electrolyte body; a housing into which the sensor element is inserted; and an element cover arranged at the tip-end side of the housing. In the gas sensor: the element cover has an inner cover arranged so as to cover the tip-end portion of the sensor element from outside, and an outer cover arranged so as to cover the inner cover from outside; and when L is defined as an axial distance from a base end of an internal space of the inner cover to a base end of the measurement electrode, an axial distance from the base end of the internal space of the inner cover to a base end of an inner vent hole positioned in the most base-end side among the inner vent holes provided to the inner cover is 0.2L to 0.65L.

Advantageous Effects of the Invention

In the gas sensor, the axial distance between the base end of the internal space of the inner cover, and the base end of an inner vent hole positioned in the most base-end side is 0.2L to 0.65L. That is, the inner vent hole is provided further on the tip-end side than the base end of the internal space is, and sufficiently apart from the measurement electrode toward the base-end side. Accordingly, when the air penetrates into the inner space of the inner cover from between the sensor element and the housing, further movement of the air toward the measurement electrode can be prevented. That is, the movement of the air toward the tip-end side can be prevented by the gas to be measured flowing into the internal space from outside through the inner vent hole. As a result, the oxygen concentration in the gas to be measured on the surface of the measurement electrode is prevented from being changed, and the detection accuracy of the gas sensor is improved.

As described above, according to the present disclosure, a gas sensor is provided which is capable of reducing the influence of the air leakage at a seal portion arranged between a sensor element and a housing to improve detection accuracy.

DESCRIPTION OF THE PREFERRED EMBODIMENTS

The gas sensor is used by being mounted to, for example, an exhaust system of an internal combustion engine or the like for vehicles.

In the present specification, a direction along which the gas sensor is inserted into the exhaust system or the like is referred to as tip-end side, and a direction opposite thereto is referred to as base-end side. Unless particularly referred to, the term axial direction indicates the axial direction of the gas sensor.

Embodiment

First Embodiment

Figure 1:
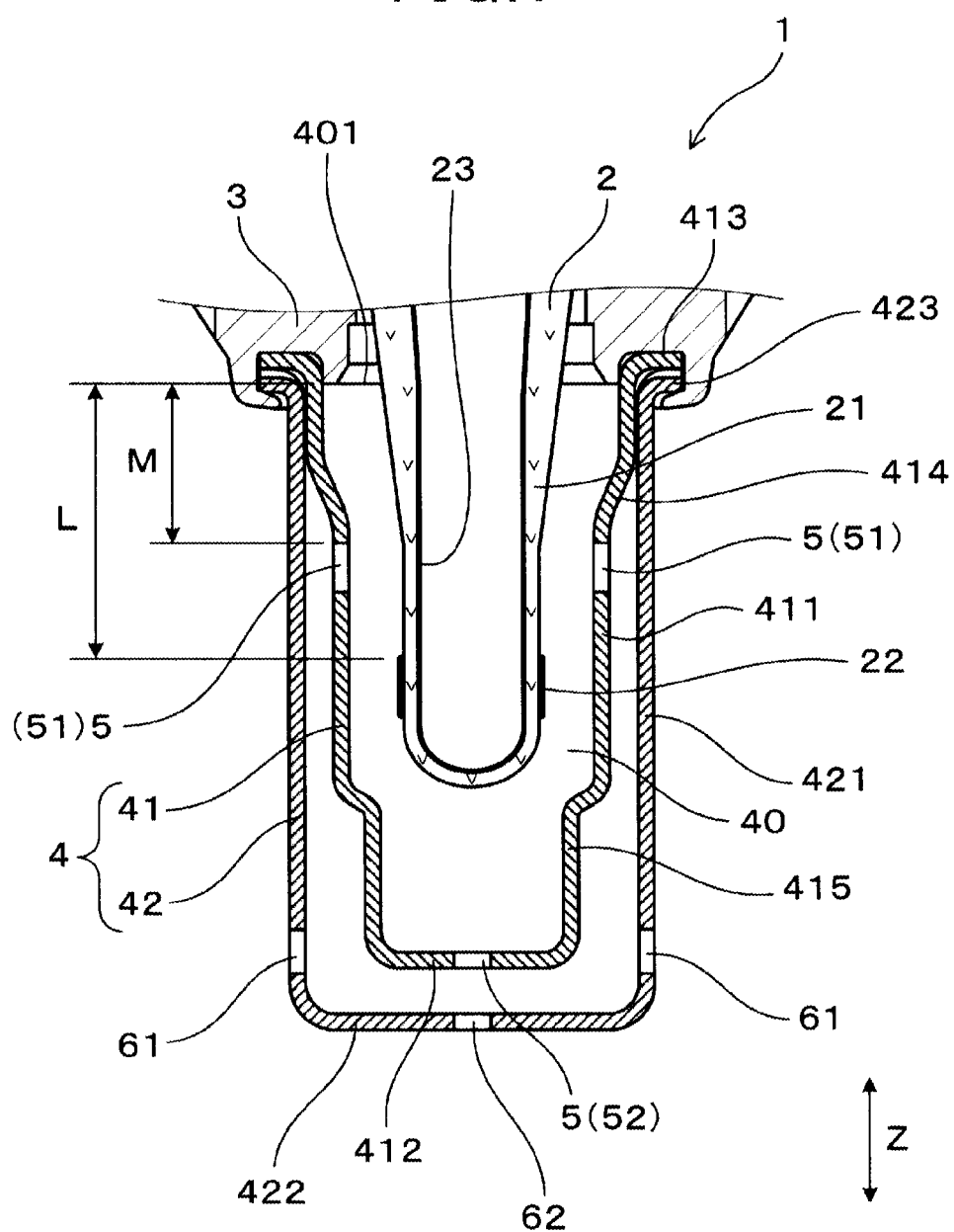
FIG. 1 is a cross-sectional view illustrating the vicinity of an element cover of a gas sensor according to a first embodiment of the present disclosure.
Figure 2:
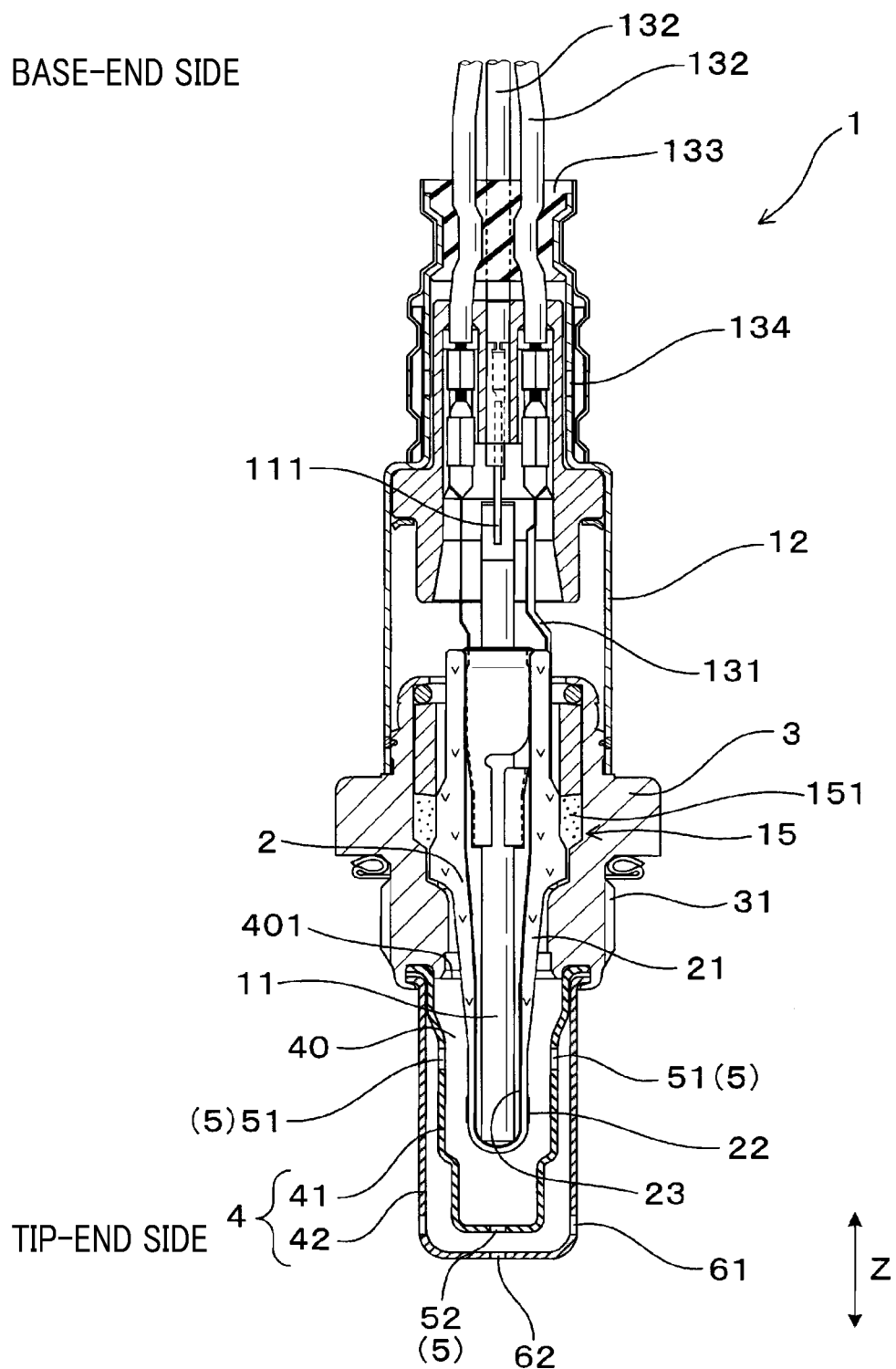
FIG. 2 is a cross-sectional view illustrating the gas sensor according to the first embodiment.
Figure 3:
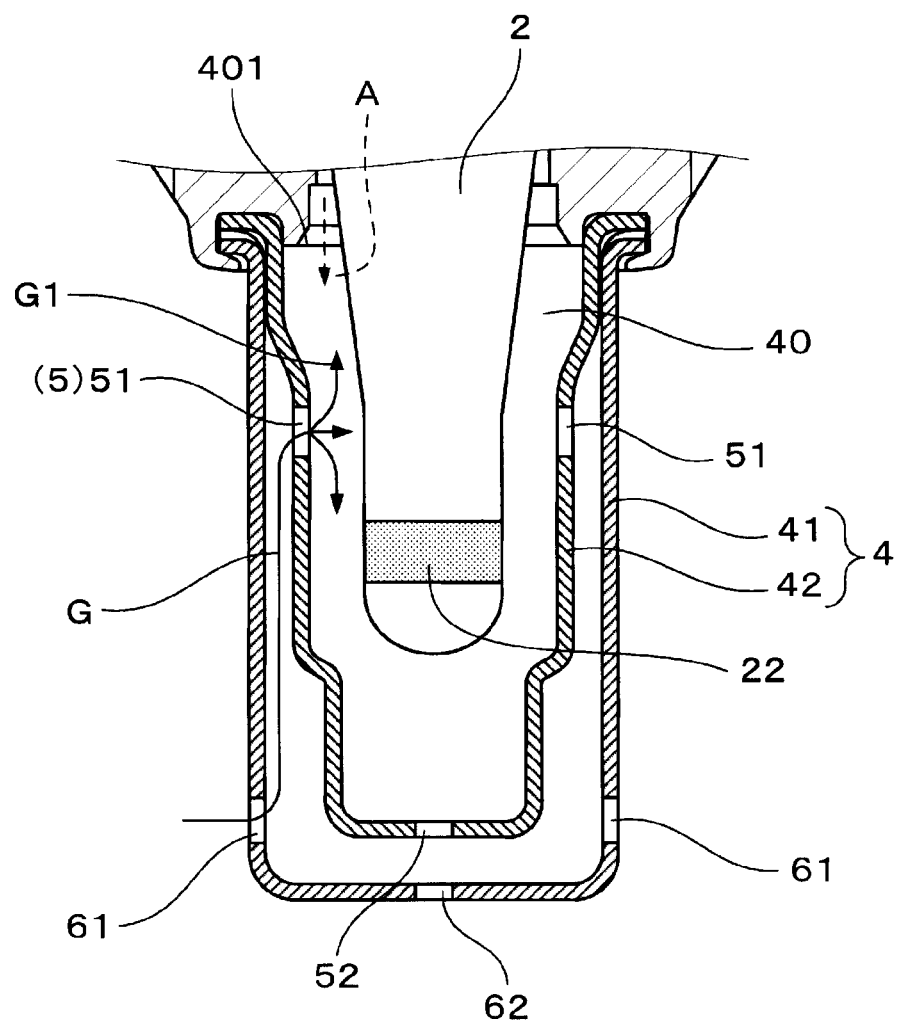
FIG. 3 is a partial cross-sectional view illustrating the vicinity of the element cover of the gas sensor according to the first embodiment.

With reference to FIGS. 1 to 3, some embodiments of the gas sensor will be described.

As shown in FIGS. 1 and 2, a gas sensor 1 of the present embodiment includes a sensor element 2, a housing 3 into which the sensor element 2 is inserted, and an element cover 4 arranged at the tip-end side of the housing 3. The sensor element 2 has a solid electrolyte body 21 having oxygen ion conductivity, and a measurement electrode 22 and a reference electrode 23 respectively provided to one surface and the other surface of the solid electrolyte body 21.

The element cover 4 has an inner cover 41 arranged so as to cover the tip-end portion of the sensor element 2 from outside, and an outer cover 42 arranged so as to cover the inner cover 41 from outside.

As shown in FIG. 1, when L is defined as the axial distance from a base end 401 of an internal space 40 of the inner cover 41 to the base end of the measurement electrode 22, M is defined as the axial distance from the base end 401 of the internal space 40 of the inner cover 41 to the base end of an inner vent hole 5 (inner side-surface hole 51) positioned in the most base-end side among the inner vent holes 5 positioned in the inner cover 41. The axial distance M is 0.2L to 0.65L. That is, the axial distances M and L of the gas sensor 1 satisfy $0.2 \leq M/L \leq 0.65$. The base end 401 of the internal space 40 is the tip end of the housing 3 inside the inner cover 41.

The inner cover 41 has the inner side-surface hole 51 as the inner vent hole 5 at an inner side-wall portion 411 formed along an axial direction Z. The outer cover 42 has an outer side-surface hole 61 at an outer side-wall portion 421 formed along the axial direction Z. The outer side-surface hole 61 is positioned further on the tip-end side than the inner side-surface hole 51 is.

As shown in FIG. 2, the sensor element 2 is in a cup shape that is a bottomed cylindrical shape which is closed at the tip-end side, and opened at the base-end side. That is, the solid electrolyte body 21 is in a cup shape that is a bottomed cylindrical shape. The measurement electrode 22 is formed at the outer surface of the sensor element 2, and the reference electrode 23 is formed at the inner surface thereof.

A main component of the solid electrolyte body 21 is zirconia. The measurement electrode 22 and the reference electrode 23 are both preferably formed of platinum group elements, and specifically formed of platinum in the present embodiment.

The reference electrode 23 is formed over substantially the entire surface of the inner surface of the solid electrolyte body 21. On the other hand, the measurement electrode 22 is provided to a portion of the solid electrolyte body 21, so as to be located in the vicinity of the tip-end portion thereof. However, in the present embodiment, the tip end of the measurement electrode 22 is positioned further at the base-end side than the tip end of the solid electrolyte body 21 is. Further, the measurement electrode 22 is formed throughout the circumference of the sensor element 2.

As shown in FIG. 2, the gas sensor 1 is configured by fixing an atmospheric air-side cover 12 to the housing 3 on base-end side. The base-end side of the sensor element 2 is opened inside the atmospheric air-side cover 12. In the base-end portion of the sensor element 2, a terminal member 131 is arranged, being electrically connected to the measurement electrode 22 and the reference electrode 23. A heater 11 for heating the sensor element 2 is arranged inside the sensor element 2. Leads 132 each formed of a coated lead wire are connected to the terminal member 131 and a terminal portion 111 of the heater 11. The leads 132 are led out from the base-end portion of the atmospheric air-side cover 12 to the outside through a bush 133. The atmospheric air-side cover 12 includes an atmospheric air introduction portion 134 for introducing the atmospheric air (air), as a reference gas, from the outside to the internal space. The air is led to the internal space of the atmospheric air-side cover 12 through the atmospheric air introduction portion 134, while being removed with moisture and the like, further led to the inside of the sensor element 2, and reaches the surface of the reference electrode 23.

A sealing member 151 filled with talc is provided to a seal portion 15 arranged between the sensor element 2 and the housing 3. Thus, the air led to the internal space of the atmospheric air-side cover 12 is sealed so as not to leak from between the sensor element 2 and the housing 3 to the tip-end side of the housing 3, that is, the internal space 40 of the element cover 4.

The seal portion 15 arranged between the sensor element 2 and the housing 3 has airtightness of an extent that allows air leakage to be 0.005 ml/min to 5 ml/min when an air pressure of 1 MPa is applied. That is, the airtightness is ensured by using an air leak tester to measure the amount of air per unit time that is leaked to measurement gas side (internal space 40 side) through the seal portion 15 when air is supplied to the seal portion 15 at a pressure of 1 MPa from an atmospheric air-side space (internal space of the atmospheric air-side cover 12). A mounting screw portion 31 for attaching the gas sensor 1 to an exhaust pipe or the like is formed at the housing 3.

As shown in FIG. 1, the element cover 4 is crimped and fixed to the tip-end portion of the housing 3, in flange portions 413 and 423 at the base end of the element cover 4. The inner cover 41 and the outer cover 42 are crimped and fixed to the housing 3 in a state where the flange portions 413 and 423 thereof are overlapped with each other.

In the inner cover 41, an inclined surface portion 414 is provided between the flange portion 413 and the inner side-wall portion 411. The inner side-surface hole 51 is formed in the inner side-wall portion 411 so as to be located at a position closer to the tip-end side than the inclined surface portion 414 is. That is, the inner side-surface hole 51 is formed at a position between the inclined surface portion 414 and the measurement electrode 22 in the axial direction Z. As shown in FIG. 3, several inner side-surface holes 51 are formed at regular intervals in the circumferential direction.

The tip-end side of the inner side-wall portion 411 is provided with a reduced-diameter portion 415 in which the diameter is reduced. Further, the tip-end side of the reduced-diameter portion 415 is provided with an inner bottom wall portion 412 which is substantially perpendicular to the axial direction. The inner bottom wall portion 412 is formed with an inner bottom-surface hole 52 as the inner vent hole 5.

As shown in FIG. 1, the outer side-wall portion 421 of the outer cover 42 is formed so as to extend from the flange portion 423 toward the tip end. Further, an outer bottom wall portion 422 is formed so as to be connected to the tip end of the outer side-wall portion 421 and perpendicular to the axial direction Z. Several outer side-surface holes 61 formed in the outer side-wall portion 421 are located closer to the tip-end side than the inner side-surface holes 51 are, while being closer to the tip-end side than the tip-end portion of the sensor element 2 is, and arranged at regular intervals in the circumferential direction.

An outer bottom-surface hole 62 is formed in the outer bottom wall portion 422. All of the inner bottom-surface hole 52, the outer bottom-surface hole 62, the inner side-surface holes 51 and the outer side-surface holes 61 are circular holes.

As shown in FIG. 1, a clearance is formed between the inner side-wall portion 411 and the outer side-wall portion 421. A clearance is also formed between the inner bottom wall portion 412 and the outer bottom wall portion 422.

The inner side-wall portion 411 and the outer side-wall portion 421 are in a substantially cylindrical shape, and formed parallel to the outer peripheral surface of the bottomed cylindrically-shaped sensor element 2, enabling shared use of the central axis of the sensor element 2.

The gas sensor 1 according to the present embodiment is a rear gas sensor arranged downstream of a catalytic filter in the exhaust system of the internal combustion engine. The gas sensor 1 according to the present embodiment is of a limiting current type that outputs a limiting current value relying on a specific gas concentration (oxygen concentration) in a gas (exhaust gas) to be measured, by applying a predetermined voltage across the measurement electrode 22 and the reference electrode 23.

That is, the gas sensor 1 is arranged in the exhaust system of the vehicle engine so as to be located downstream of the catalytic filter that purifies the exhaust gas. Thus, the gas sensor 1 outputs a limiting current value which relies on the oxygen concentration in the exhaust gas which has passed through the catalytic filter. It is so configured that, based on the acquired limiting current value, an air-fuel ratio of the air-fuel mixture supplied to the internal combustion engine is calculated to feed back the calculated ratio to the engine control system.

Next, advantageous effects of the present embodiment will be described.

In the sensor element 2, the axial distance M between the base end 401 of the internal space 40 and the base end of each inner side-surface hole 51 is 0.2L to 0.65L. That is, each inner side-surface hole 51 is provided at a position further on the tip-end side than the base end 401 of the internal space 40 is, while being sufficiently apart from the measurement electrode 22 toward the base-end side. Accordingly, as shown in FIG. 3, when air A penetrates into the internal space 40 of the inner cover 41 from between the sensor element 2 and the housing 3, the air A is prevented from further moving toward the measurement electrode 22. That is, the movement of the air A toward the tip end can be prevented by the gas G to be measured flowing into the internal space 40 from outside through the inner side-surface holes 51. As a result, the oxygen concentration in the gas G to be measured on the surface of the measurement electrode 22 is prevented from being changed, and the detection accuracy of the gas sensor 1 is improved.

The outer side-surface holes 61 are positioned further at the tip-end side than the inner side-surface holes 51 are. Thus, when the gas G to be measured is introduced from between the outer cover 42 and the inner cover 41 through the outer side-surface holes 61, an airflow is generated, which flows from the outer side-surface holes 61 toward the inner side-surface holes 51. Thus, also, when the gas G to be measured flows into the internal space 40 from the inner side-surface holes 51, an airflow is likely to be generated which flows toward the base end. That is, this means that an airflow G1 flowing toward the base-end 401 of the internal space 40 is also present in the vicinity of the inner side-surface holes 51 in the internal space 40. Accordingly, if the air A leaks from the base end 401 into the internal space 40, the airflow G1 can push back the air A toward the base end. As a result, the air A can be prevented from moving to the vicinity of the measurement electrode 22. Thus, since the outer side-surface holes 61 are located further at the tip-end side than the inner side-surface holes 51 are, the influence of the air leakage from between the sensor element 2 and the housing 3 is effectively prevented.

The gas sensor 1 is a rear gas sensor arranged downstream of a catalytic filter in the exhaust system of the internal combustion engine. Thus, even though the level of detection accuracy especially required of the gas sensor 1 is high, the configuration described above can satisfy the requirement.

Since the gas sensor 1 is of a limiting current type, high detection accuracy (stoichiometric air-fuel ratio accuracy) can be obtained.

As described above, the present embodiment can provide a gas sensor which is capable of reducing the influence of the air leakage in a seal portion arranged between a sensor element and a housing to improve detection accuracy.

Second Embodiment

Figure 4:
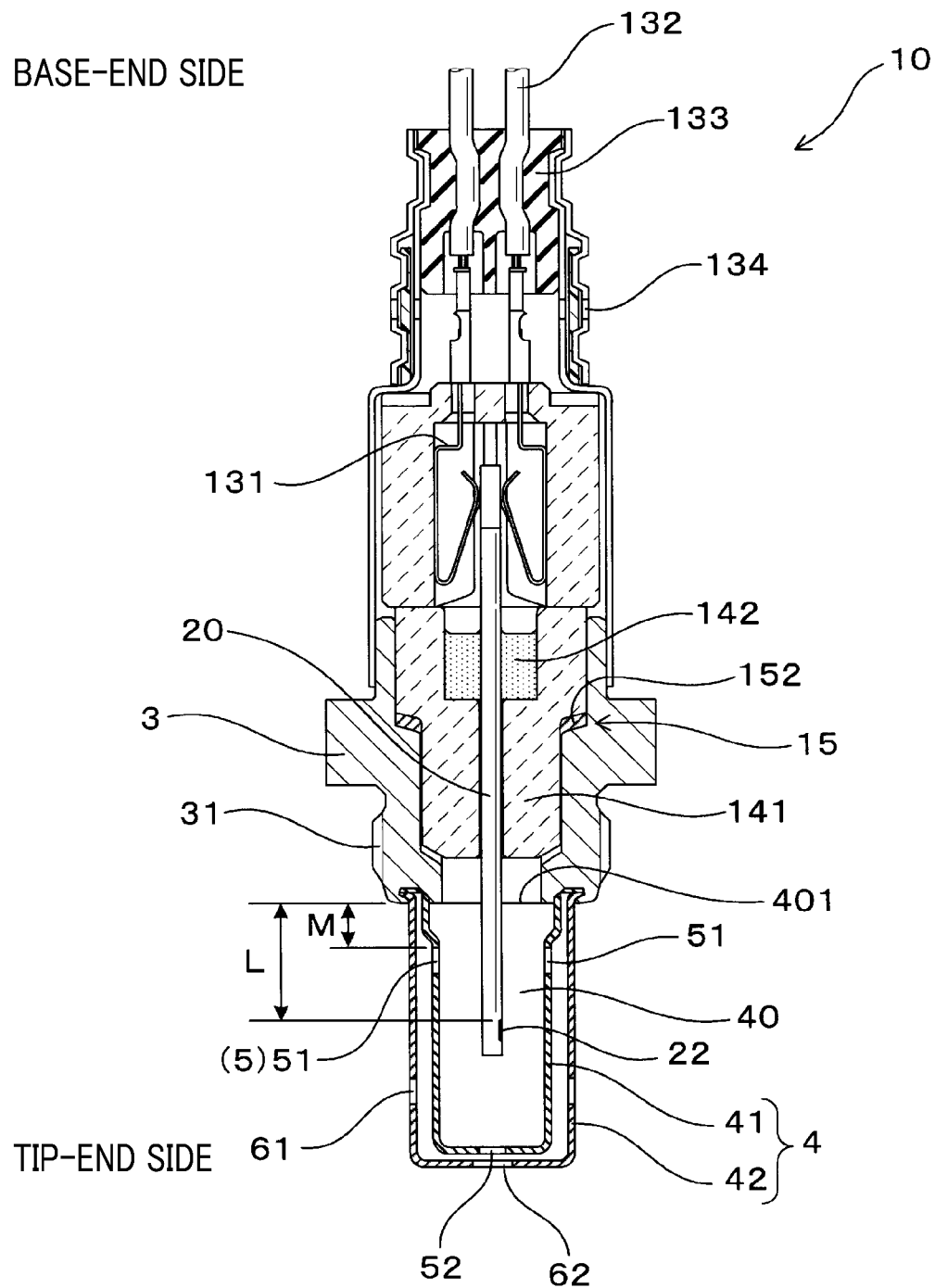
FIG. 4 is a cross sectional view illustrating a gas sensor according a second embodiment.

As shown in FIG. 4, the present embodiment is an example of a gas sensor 10 using a laminated sensor element 20.

That is, the sensor element 20 in the gas sensor 10 of the present embodiment is in a plate bar-like shape, and the tip-end portion thereof is arranged inside the element cover 4. The sensor element 20 is formed by laminating other ceramic layers in a thickness direction of a plate-like solid electrolyte body. A heater (not shown) is also integrated into the sensor element 20. At the tip-end portion of the sensor element 20, a measurement electrode 22 is provided. A reference electrode (not shown) is formed inside the sensor element 20.

The sensor element 20 is internally held in a housing 3 through an insulator 141. That is, the sensor element 20 is held by the insulator 141 by being inserted therein, and the insulator 141 is held by the housing 3 by being inserted therein. A part between the sensor element 20 and the insulator 141 is sealed by a glass seal portion 142.

A part between the insulator 141 and the housing 3 is provided with a ring-like sealing member 152. The sealing member 152 prevents leakage of air from between the insulator 141 and the housing 3, or from between the sensor element 20 and the housing 3. In the present embodiment, a seal portion 15 arranged between the sensor element 20 and the housing 3 is located between the insulator 141 and the housing 3, and thus the airtightness is designed to be ensured by the sealing member 152.

The gas sensor 10 of the present embodiment has substantially the same configuration and functions as the gas sensor 1 of the first embodiment. Unless particularly indicated, the reference signs used in the present embodiment and the drawings relating to the present embodiment represent the same components as those in the first embodiment.

In the gas sensor 10 of the present embodiment as well, the element cover 4 has an inner cover 41 and an outer cover 42. The inner cover 41 has an inner vent hole 5 (inner side-surface holes 51 and inner bottom-surface hole 52), and the outer cover 42 has outer side-surface holes 61 and an outer bottom-surface hole 62. The shapes of the inner cover 41 and the outer cover 42 are partially different from the shapes described in the first embodiment. However, the shapes described in the first embodiment can also be applied to the present embodiment.

The axial distance M from the base end 401 of the internal space 40 of the inner cover 41 to the base end of the inner vent hole 5 (inner side-surface holes 51) positioned in the most base-end side among the inner vent holes 5 positioned in the inner cover 41 is 0.2L to 0.65L. Herein, similar to the first embodiment, L is an axial distance from the base end 401 of the internal space 40 of the inner cover 41 to the base end of the measurement electrode 22.

The gas sensor 10 provided with the laminated sensor element 20 of the present embodiment can also obtain advantageous effects similar to those of the first embodiment.

Experimental Example

Figure 5:
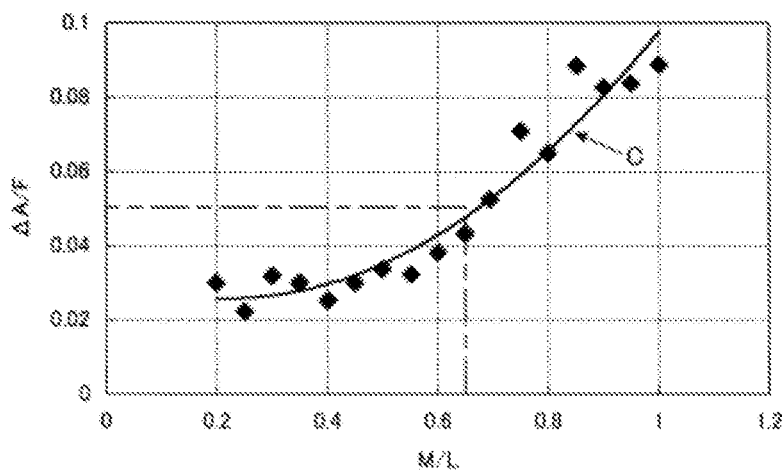
FIG. 5 is a graph illustrating a relationship between M/L and deviation of stoichiometric air-fuel ratio ($\Delta$A/F) according to an experimental example.

As shown in FIG. 5, in the present example, the relationship was found out between the ratio (M/L) of the axial distance M to the axial distance L described in the first embodiment, and the detection accuracy of the gas sensor.

The gas sensor used as a sample had the same basic configuration as that of the gas sensor 1 of the first embodiment. The axial distance M was variously changed by variously changing the position of the inner side-surface holes 51 along the axial direction Z to prepare various types of gas sensors. In the gas sensor of the present example, the dimension of each portion of the element cover 4, the position of the measurement electrode 22 of the sensor element 2, and the like are as follows.

The axial distance L from the base end 401 of the internal space 40 to the base end of the measurement electrode 22 was set to 9.3 mm. The axial length of the measurement electrode 22 was set to 2 mm. The axial distance from the base end 401 to the tip end of the inner cover 41 was set to 20 mm. The axial distance from the base end 401 to the tip end of the outer cover 42 was set to 22.5 mm. The axial distance from the base end 401 to the base end of the outer side-surface holes 61 was set to 18.5 mm. Six inner side-surface holes 51 each having a circular shape and a diameter of 2 mm were formed. Six outer side-surface holes 61 each having a circular shape and a diameter of 2 mm were formed. One inner bottom-surface hole 52 in a circular shape of 2 mm diameter was formed, and one outer bottom-surface hole 62 in a circular shape of 2 mm diameter was formed. The thickness of both the inner cover 41 and the outer cover 42 was 0.5 mm. A clearance between the inner side-wall portion 411 and the outer side-wall portion 421 was set to 2 mm. The airtightness of the seal portion 15 was of a degree at which an amount of air leakage with the application of air pressure of 1 MPa was 0.01 ml/min.

In the experiment, the gas sensor was arranged at an exhaust pipe of an in-line four-cylinder gasoline engine (internal combustion engine) with a displacement of 2.4L. Then, the air-fuel mixture of a stoichiometric air-fuel ratio (A/F=14.6) was supplied to a combustion chamber, and the engine was operated at a speed of 2000 rpm. At this time, the air-fuel ratio (A/F) was detected from the limiting current flowing through the gas sensor to which a predetermined voltage was applied.

Then, deviation of the detected A/F value from the stoichiometric air-fuel ratio (A/F=14.6) (stoichiometric air-fuel ratio deviation $\Delta A/F$) was evaluated. That is, the measured value A/F was evaluated as to what extent it was higher than the stoichiometric air-fuel ratio due to the influence of the air leakage from the seal portion 15. In this case, a generally desired stoichiometric air-fuel ratio of 0.05 or less was set as a target value.

The evaluation is shown in FIG. 5. Several plots shown in the graph of FIG. 5 are actual measurements, and the curve C is an approximate curve based on these actual measurements. As will be understood from FIG. 5, the stoichiometric air-fuel ratio deviation ($\Delta A/F$) tended to be lower, as M/L became lower. As can be seen, $\Delta A/F \leq 0.05$ was achieved by setting M/L to 0.65 or less. Also, when $0.2 \leq M/L \leq 0.65$ was satisfied, $\Delta A/F \leq 0.05$ was always achieved.

As will be understood from these results, the influence of the air leakage in the seal portion 15 is reduced when $0.2 \leq M/L \leq 0.65$ is satisfied, thereby improving the detection accuracy of the gas sensor.

REFERENCE SIGNS LIST 1, 10: Gas sensor
2, 20: Sensor element
3: Housing
4: Element cover
40: Internal space
401: Base end (of internal space)
41: Inner cover
42: Outer cover
5: Inner vent hole

What is claimed is:
1. A gas sensor comprising:
a sensor element including a solid electrolyte body having oxygen ion conductivity, and a measurement electrode and a reference electrode respectively provided to one surface and the other surface of the solid electrolyte body;
a housing into which the sensor element is inserted; and
an element cover arranged at a tip-end side of the housing, wherein:
the element cover has an inner cover arranged so as to cover a tip-end portion of the sensor element from outside, and an outer cover arranged so as to cover the inner cover from outside;
when L is defined as an axial distance from a base end of an internal space of the inner cover to a base end of the measurement electrode, an axial distance from the base end of the internal space of the inner cover to a base end of an inner vent hole positioned in the most base-end side among the inner vent holes provided to the inner cover is 0.2L to 0.65L;

the inner cover has inner side-surface holes as the inner vent hole at an inner side-wall portion formed along an axial direction, and the outer cover has outer side-surface holes at an outer side-wall portion formed along the axial direction, all of the outer side-surface holes being positioned further on a tip-end side than any of the inner side-surface holes is;

a tip end clearance is formed between a tip-end portion of the inner cover and a tip-end portion of the outer cover;

a side wall clearance is formed between the outer side-wall portion and the inner side-wall portion; and the tip end clearance is larger than the side wall clearance.

2. The gas sensor according to claim 1, wherein a seal portion arranged between the sensor element and the housing has airtightness of an extent that allows air leakage to be 0.005 ml/min to 5 ml/min when an air pressure of 1 MPa is applied.

3. The gas sensor according to claim 1, wherein the gas sensor is of a limiting current type that outputs a limiting current value relying on a specific gas concentration in a gas to be measured, by applying a predetermined voltage across the measurement electrode and the reference electrode.

4. The gas sensor according to claim 1, wherein the gas sensor is a rear gas sensor arranged downstream of a catalytic filter in an exhaust system of an internal combustion engine.

5. A gas sensor comprising:

a sensor element including a solid electrolyte body having oxygen ion conductivity, and a measurement electrode and a reference electrode respectively provided to one surface and the other surface of the solid electrolyte body;

a housing into which the sensor element is inserted; and an element cover arranged at a tip-end side of the housing, wherein:

the element cover has an inner cover arranged so as to cover a tip-end portion of the sensor element from outside, and an outer cover arranged so as to cover the inner cover from outside;

when L is defined as an axial distance from a base end of an internal space of the inner cover to a base end of the measurement electrode, an axial distance from the base end of the internal space of the inner cover to a base end of an inner vent hole positioned in the most base-end side among the inner vent holes provided to the inner cover is 0.2L to 0.65L;

the inner cover has inner side-surface holes as the inner vent hole at an inner side-wall portion formed along an axial direction, and the outer cover has outer side-surface holes at an outer side-wall portion formed along the axial direction, all of the outer side-surface holes being positioned further on a tip-end side than any of the inner side-surface holes is; and a tip end clearance is formed between an inner bottom wall portion of the inner cover and an outer bottom wall portion of the outer cover such that the inner bottom wall portion of the inner cover and the outer bottom wall portion of the outer cover are spaced apart.

6. The gas sensor according to claim 5, wherein:

the inner side-surface holes are defined in the inner cover at a base-end side of the inner side-wall portion; and the inner side-wall portion has a tip-end side having a smaller diameter than a diameter of the base-end side of the inner side-wall portion so that a side wall clearance formed between the tip-end side of the inner side-wall portion and the outer side-wall portion is larger than a side wall clearance formed between the base-end side of the inner side-wall portion and the outer side-wall portion.

* * * * *